(12) United States Patent
Serafini et al.

(10) Patent No.: US 10,888,590 B2
(45) Date of Patent: Jan. 12, 2021

(54) MEDICATED PROPOLIS OIL COMPOSITION

(71) Applicant: MatrixMed Inc., New York, NY (US)

(72) Inventors: Randal Alexander Serafini, New York, NY (US); Shiv Krishnan, Memphis, TN (US); Jonathan Patrick Masterson, IV, Long Beach, CA (US)

(73) Assignee: MatrixMed Inc., New York, NY (US)

( * ) Notice: Subject to any disclaimer, the term of this patent is extended or adjusted under 35 U.S.C. 154(b) by 123 days.

(21) Appl. No.: 16/042,171

(22) Filed: Jul. 23, 2018

(65) Prior Publication Data

US 2019/0022149 A1    Jan. 24, 2019

Related U.S. Application Data

(60) Provisional application No. 62/535,451, filed on Jul. 21, 2017.

(51) Int. Cl.

| | | |
|---|---|---|
| *A61K 9/107* | (2006.01) |
| *A61K 35/644* | (2015.01) |
| *A61K 9/70* | (2006.01) |
| *A61K 47/44* | (2017.01) |
| *A61K 47/26* | (2006.01) |
| *A61K 31/167* | (2006.01) |
| *A61P 17/02* | (2006.01) |
| *A61K 31/135* | (2006.01) |
| *A61K 31/04* | (2006.01) |
| *A61K 9/06* | (2006.01) |
| *A61K 9/12* | (2006.01) |
| *A61K 31/165* | (2006.01) |
| *A61K 9/00* | (2006.01) |
| *A61K 47/02* | (2006.01) |
| *A61K 45/06* | (2006.01) |

(52) U.S. Cl.
CPC .......... *A61K 35/644* (2013.01); *A61K 9/0014* (2013.01); *A61K 9/0021* (2013.01); *A61K 9/06* (2013.01); *A61K 9/12* (2013.01); *A61K 9/122* (2013.01); *A61K 9/7007* (2013.01); *A61K 9/7015* (2013.01); *A61K 31/04* (2013.01); *A61K 31/135* (2013.01); *A61K 31/165* (2013.01); *A61K 31/167* (2013.01); *A61K 45/06* (2013.01); *A61K 47/02* (2013.01); *A61K 47/26* (2013.01); *A61K 47/44* (2013.01); *A61P 17/02* (2018.01)

(58) Field of Classification Search
None
See application file for complete search history.

(56) References Cited

U.S. PATENT DOCUMENTS

| | | |
|---|---|---|
| 3,751,562 A | 8/1973 | Nichols et al. |
| 4,643,918 A | 2/1987 | Orban |
| 4,748,022 A | 5/1988 | Busciglio |
| 4,752,536 A | 6/1988 | Shimizu |
| 5,002,974 A | 3/1991 | Geria |
| 5,186,984 A | 2/1993 | Gabbed |
| 5,302,415 A | 4/1994 | Gabara et al. |
| 6,197,305 B1 | 3/2001 | Friedman et al. |
| 6,645,507 B2 | 11/2003 | Bettle et al. |
| 6,645,510 B1 | 11/2003 | Coury et al. |
| 2003/0104018 A1 | 6/2003 | Griscom Bettie et al. |

FOREIGN PATENT DOCUMENTS

| | | |
|---|---|---|
| DE | 639287 C | 12/1936 |
| GB | 927115 A | 5/1963 |
| WO | 9216589 A1 | 10/1992 |
| WO | WO-2004022034 A1 * | 3/2004 ......... A61K 2300/00 |

OTHER PUBLICATIONS

Banskota AH, Tezuka Y, Adnyana K, Midorikawa K, Matsushige K, Message D, Huertas AAG, Kadota S. Cytotoxic, hepatoprotective and free radical scavenging effects of propolis from Brazil, Peru, the Netherlands and China. Journal of Ethnopharmacology. 2000; 73(1-2):239-246.

Marcucci MC. Propolis: chemical composition, biological properties and therapeutic activity. Apidologie. 1995; 26 (2)-83-99.

Oryan A, Alemzadeh E, Moshiri A. Potential role of propolis in wound healing: Biological properties and therapeutic activities. Biomedicine and Pharmacotherapy. 2018; 98:469-483.

Castaldo S, Capasso F. Propolis, an old remedy used in modern medicine. Fitoterapia. 2002; 73:S1-S6.

Han MC, Durmus AS, Karabulut E, Yaman I. Effects of Turkish Propolis and Silver Sulfadiazine on Burn Wound Healing in Rats. Revue de médecine vétérinaire. 2005; 156(12):624-627.

Pillai SI, Palsamy P, Subramanian S, Kandaswamy M. Wound healing properties of Indian propolis studied on excision wound-induced rats. Pharmaceutical Biology. 2010; 41(11):1198-1206.

Ibrahim NA. Evaluation of the effect of bee propolis cream on wound healing in experimentally induced type 1 diabetes mellitus: a histological and immunohistochemical study. The Egyptian Journal of Histology. 2013; 36: 847-856.

Henshaw FR, Bolton T, Nube V, Hood A, Veldhoen D, Pfrunder L, Mckew GL, Macleod C, Mclennan SV, Twigg SM. Topical application of the bee hive protectant propolis is well tolerated and improves human diabetic foot ulcer healing in a prospective feasibility study. Journal of Diabetes and Its Complications. 2014; 28:850-857.

Kucharzewski M, Kozka M, Urbanek T. Topical Treatment of Nonhealing Venous Leg Ulcer with Propolis Ointment. Evidence-Based Complementary and Alternative Medicine. 2013.

Nevin KG, Rajamohan T. Effect of Topical Application of Virgin Coconut Oil on Skin Components and Antioxidant Status during Dermal Wound Healing in Young Rats. Skin Pharmacology and Physiology. 2010; 23:290-297.

Srivastava P. and Durgaprasad S. Burn wound healing property of Cocos nucifera: An appraisal. Indian Journal of Pharmacology. 2008; 40(4):144-146.

(Continued)

*Primary Examiner* — Susan T Tran
(74) *Attorney, Agent, or Firm* — Brian P. Harrod; George W. Moxon, II

(57) ABSTRACT

The present invention is directed to a medicated oil composition comprising propolis, about 1-40% by weight, a carrier, about 30-90% by weight, an analgesic, about 0.1-10% by weight, a surfactant, about 0.25-20% by weight, and a diluent, about 5-50% by weight.

3 Claims, 9 Drawing Sheets

(56) References Cited

OTHER PUBLICATIONS

Rosenblatt J, Reitzel RA, Raad I. Caprylic Acid and Glyceryl Trinitrate Combination for Eradication of Biofilm. Antimicrobial Agents and Chemotherapy. 2015; 59(3):1786-1788.

Magalhaes MSF, Fechine FV, Nogueira De Macedo R, Monteiro DLS, Oliveira CC, Brito GAC, Amaral De Moraes ME, Odorico De Moraes M. Effect of a combination of medium chain triglycerides, linoleic acid, soy lecithin and vitamins A and E on wound healing in rats. Acta Cirurgica Brasileira. 2008; 23(3)262-269.

Ferreira AM, Vieira De Souza BM, Rigotti MA, Loureiro MRD. The use of fatty acids in wound care: an integrative review of Brazilian literature. Revista de Escola de Engermagem da USP. 2012; 46(3):745-753.

Yuan JS, Ansari M, Samaan M, Acosta EJ. Linker-based lecithin microemulsions for transdermal delivery of idocaine. International Journal of Pharmaceutics. 2008; 349(1-2)130-143.

Gaufberg SV, Walta MJ, Workman TP. Expanding the use of topical anesthesia in wound management: sequential layered application of topical lidocaine with epinephrine. The American Journal of Emergency Medicine. 2007; 25(4):379-384.

Sinclair R, Cassuto J, Hogstrom S, Linden I, Faxen A, Hedner T, Ekman R. Topical anesthesia with idocaine aerosol in the control of postoperative pain. Anesthesiology. 1988; 68(6):895-901.

Trial C, Darbas J, Lavigne JP, Sotto A, Simoneau G, Tillet Y, Leot L. Assessment of the antimicrobial effectiveness of a new silver alginate wound dressing: a RCT. Journal of Wound Care. 2010; 19(1):20-26.

Beele H, Meuleneire F, Nahuys M, Percival SL. A prospective randomised open label study to evaluate the potential of a new silver alginate/carboxymethylcellulose antimicrobial wound dressing to promote wound healing. International Wound Journal. 2010; 7(4):262-270.

Percival SL, Slone W, Linton S, Okel T, Corum L, Thomas JG. The antimicrobial efficacy of a silver alginate dressing against a broad spectrum of clinically relevant wound isolates. International Wound Journal. 2011; 8 (3):237-243.

Bascom J. Pilonidal disease: Long-term results of follicle removal. Diseases of the Colon & Rectum. 1983; 26 (12):800-807.

Isik A, Idiz O, Firat D. Novel Approaches in Pilonidal Sinus Treatment. Prague Medical Report. 2016; 117 (4):145-152.

Chintapatla S, Safarani N, Kumar S, Haboubi N. Sacrococcygeal pilonidal sinus: historical review, pathological insight and surgical options. Techniques in Colopractology. 2003; 7:3-8.

Mccallum IJD, King PM, Bruce J. Healing by primary closure versus open healing after surgery for pilonidal sinus. Cochrane Systematic Review—Intervention. 2010.

Daneman D. Type 1 diabetes. The Lancet. 2006; 367:847-858.

Chatterjee S, Khunti K, Davies MJ. Type 2 diabetes. The Lancet. 2017; 389:2239-2251.

Debelea D, Bell RA, D'Aostino Jr, Imperatore G, Johansen GM, Linder B, Liu LL, Loots B, Marcovina S, Mayer-Davis EJ, Pettitt DJ. Incidence of diabetes in youth in the United States. JAMA. 2007; 297(24)2716-2724.

Hobizal KB, Wukich DK. Diabetic foot infections: current concept review. Diabetic Foot & Ankle. 2012; 3:18409.

Keller PA, Wille J, Van Ramshorst B, Van Der Werken C. Pressure ulcers in intensive care patients: a -eiview of risks and prevention. Intensive Care Medicine. 2002; 28:1379-1388.

Reddy M, Gill SS, Rochon PA. Preventing Pressure Ulcers: A Systematic Review. JAMA. 2006; 296(8):974-984.

Kerstein MD, Gemmen E, Van Rijswijk L, Lyder CH, Phillips T, Xakellis G, Golden K, Harrington C. Cost and Cost Effectiveness of Venous and Pressure Ulcer Protocols of Care. Disease Management and Health Outcomes. 2001; 9(11):651-663.

Duscher D, Neofytou E, Wong VW, Maan ZN, Rennert RC, Inayathullah M, Januszyk M, Rodrigues M, Malkovskiy AV, Whitmore AJ, Walmsley GG, Galvez MG, Whittam AJ, Brownlee M, Rajadas J, Gurtner GC. Transdermal deferoxamine prevents pressure-induced diabetic ulcers. PNAS. 2015; 112(1):94-99.

Stauffer VK, Luedi MM, Kauf P, Schmid M, Diekmann M, Wieferich K, Schuriger B, Doll D. Common surgical procedures in pilonidal sinus disease: A meta-analysis, merged data analysis, and comprehensive study on recurrence. Scientific Reports. 2018; 8:3058.

* cited by examiner

MEDICATED PROPOLIS OIL COMPOSITION

BACKGROUND OF THE INVENTION

The present invention is an improved treatment for pilonidal cysts, diabetic ulcers, decubitus/pressure ulcers, general post-operative infection prevention and other diseases. Pilonidal disease is a chronic skin condition characterized by the formation of an abscess or cyst, a collection of pus that has built up within tissue in the body, near the region where the tailbone meets the upper crease of the buttocks. Once formed the abscess is prone to redness and inflammation, pus and blood drainage from the abscess, and pain and itchiness while walking or sitting. Most physicians believe that pilonidal cysts are caused by ingrown hairs, and they often find hair follicles inside the cyst. Another theory is that pilonidal cysts appear after a trauma to that region of the body. The prevalence of pilonidal cysts is 26 per 100,000 with ratio of males to females being ~3:1.

Antibiotics do not heal a pilonidal cyst. Midline incisions, followed by primary closure or secondary intention healing, or off-midline incisions followed by primary closure (suturing) and drainage are the most common and preferred methods for treating a first pilonidal cyst. In secondary intention healing, which has been associated with a lower incidence of recurrence, the doctor excises unhealthy tissue, removing any hair follicles and leaves the wound open, packing the open space of the wound with gauze. An advantage is that it is a simple procedure that can be performed under local anesthesia. A disadvantage is that the patient has to change the gauze often until the cyst heals, which sometimes takes up to 3 weeks if further infection is avoided. Furthermore, the wound is prone to infection or recurrence, which can prolong the healing process to months or require further surgical intervention.

Diabetes mellitus (DM) ulcers arise due to insulin deficiency caused by autoimmune/idiopathic disorders typically found in younger populations (Type 1) or by genetic and environmental (i.e. extra weight) conditions (Type 2; milder than Type 1). While it is estimated that approximately 90% of diabetic patients have Type 2 DM, both subtypes suffer from vascular complications that can result in neuropathies. These neuropathies, in turn, can lead to a lack of sensation that leaves the patient unaware of injuries to lower extremities, such as the feet. Because these areas tend to be hypoxic in nature, these wounds can turn into ulcers and are further prone to infections. Indeed, around 15-25% of diabetic patients will suffer from diabetic foot ulceration, with one study estimating that diabetic foot ulcers can have infection rates of up to 50%. These infections lead to hospitalization and, in extreme cases, amputation. Furthermore, poor circulation renders these wounds chronic in nature, necessitating an alternate therapy for enhancement of wound healing and reduction of infection potential.

Decubitus (or pressure) ulcers are caused by skin breakdown due to bed confinement or inactivity for a long period of time, which leads to progressive skin breakdown. This condition has 4 grades associated with the intensity of the ulceration, from non-blanchable erythema of intact skin to extensive destruction with tissue necrosis. As opposed to the abovementioned conditions, pressure ulcers are more common in elderly populations, particularly those with physical impairments. It is estimated that 4-6% of these ulcers require treatment for infections. Due to the possibly chronic nature of pressure ulcers, as is seen with diabetic ulcers and pilonidal sinuses, an efficient wound healing treatment is necessary for this condition (preferable with concurrent anti-microbial capabilities).

Antibiotic resistance is a significant issue in the medical field, with methicillin-resistant *Staphylococcus aureus* (MRSA) commonly causing infections in the hospital setting. The CDC estimates that approximately 2 million people are infected with antibiotic-resistance bacteria annually in the United States alone, with 23,000 dying as a result of these infections. Many believe that four key factors are involved in preventing multidrug-resistant infections: surveillance, prevention and control, research, and product development. Therefore, a preventative measure in the hospital setting, particularly when handling open wounds such as those involved in invasive surgeries, is warranted. Many natural compounds, such as the bee product propolis, have shown activity against MRSA and several other drug-resistant bacterial species, viruses, and fungal species. Thus, natural therapeutics may be the key to significantly combating resistant infections.

Propolis is a naturally viscous substance that results from the combination of plant exudates and bee secretions. Because of the geographic variability in botanical species, the composition of propolis varies globally, necessitating the presence of standardization methods that define the presence of bioactive and preferable compounds. Some studies found that, regardless of this variability, the benefits of medical propolis use from various areas are similar. It is well known that propolis has several therapeutic benefits, including antibacterial, antiviral, antifungal, anti-inflammatory, and antioxidant activity, as well as dermatological and wound-healing benefits. It has also been suggested that propolis from specific regions may have anesthetic effects. Many believe that flavonoids are the primary bioactive compounds that contribute to these therapeutic effects, with molecules such as galangin, pinocembrin, apigenin and quercetin present within propolis. Other non-flavonoid bioactive compounds include hydroxycinnamic acids, such as caffeic acid (and its derivatives) and p-coumaric acid, which have also demonstrated therapeutic effects including anti-inflammation.

It has been known for many years that silver is a useful antibacterial agent with broad-spectrum activity together with compatibility with mammalian tissue, and there have been many proposals to incorporate silver into wound dressings to obtain the advantage of the bactericidal properties of silver in a wound dressing. In addition, silver has been applied to fibrous material previously for non-wound dressing purposes, usually for the purpose of enhancing electrical conductivity, see for example UK-A-927,115, WO-A-92/16589, DE-C-2,639,287, U.S. Pat. Nos. 5,302,415, 5,186,984, 4,752,536, 4,643,918, JP-010207473A, and JP-020153076. Silver has been applied to such fibers, which are generally not gel-forming, in a variety of ways in those references, some of which involve immersing the fibers into a silver solution, but detail of the procedures used is often lacking.

Metallic silver is also known to exhibit wound healing properties. Although metallic silver has distinct advantages, silver primarily used for wound dressings is in an ionic form (i.e., a silver salt or compound). However, the antibiotic activity provided with ionic silver from silver salts or compounds dissipate rather quickly due to the silver salts or compounds in the wound care product being dissolved by the aqueous nature of the wound environment. As a result, dressings must be replaced frequently resulting in pain or discomfort and inconvenience for the patient as the dressing is removed and replaced. Moreover, the rapid release of ionic silver can possibly lead to toxicity. Similarly, silver containing creams (e.g., including silver sulfadiazine) must be consistently reapplied to the injured area, and the dressing must be removed for reapplication of the cream. Silver salts, as well as unbound metallic silver particles, can also irritate the skin and prolonged contact can cause localized or site-specific argyria, which is characterized by a pronounced, permanent ashen-gray skin discoloration.

There is apparent need for other treatment options that will facilitate improved healing processes for pilonidal cysts and similar diseases and conditions and reduce morbidity in otherwise healthy patients. The issues with modern wound care are that there is no single intervention that 1) improves healing rates, 2) reduces pain, and 3) increases oxygenation by potentially reducing the need for heavy gauze packing.

SUMMARY OF THE INVENTION

The present invention is directed to a medicated oil composition comprising propolis, about 1-40% by weight, a carrier, about 30-90% by weight, an analgesic, about 0.1-10% by weight, a surfactant, about 0.25-20% by weight, and a diluent, about 5-50% by weight.

BRIEF DESCRIPTION OF THE DRAWINGS

The foregoing and other features and advantages of the present invention will become apparent to those skilled in the art to which the present invention relates upon reading the following description with reference to the accompanying drawings, in which like reference characters refer to like elements through the different figures and in which.

DETAILED DESCRIPTION OF THE INVENTION

Figure 1:
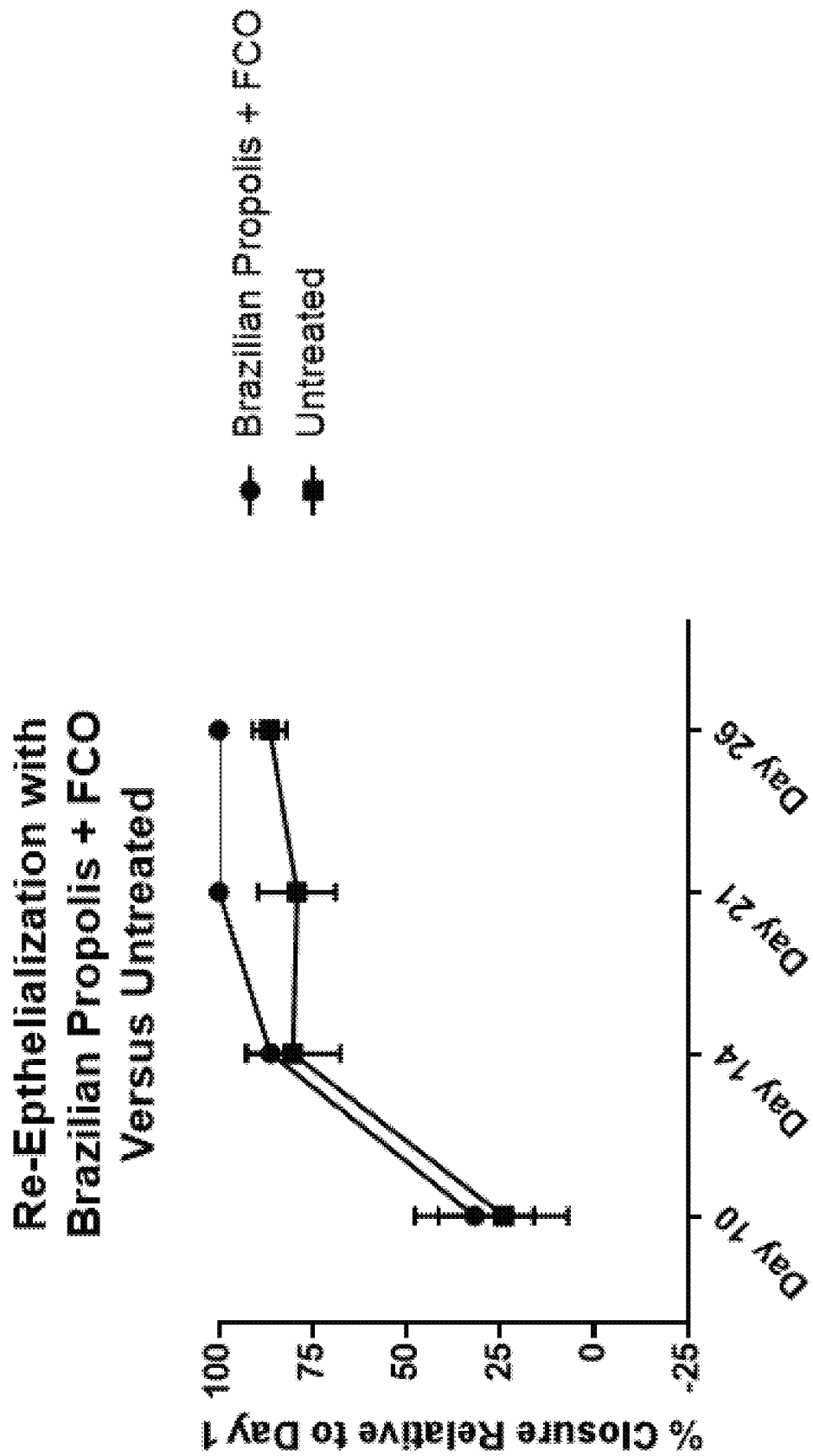
FIGS. 1-6 are graphical depiction of test results.
Figure 2:
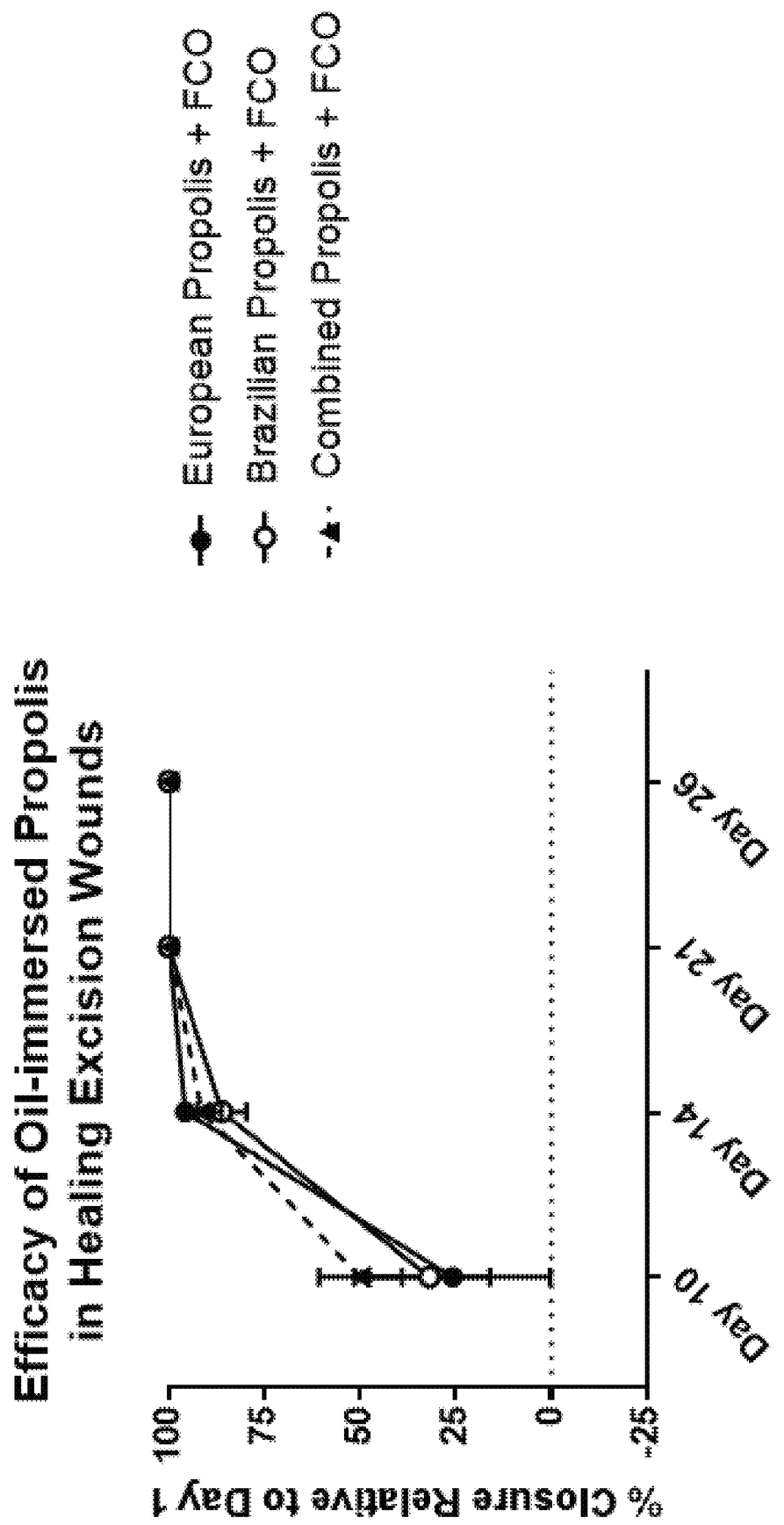
Figure 3:
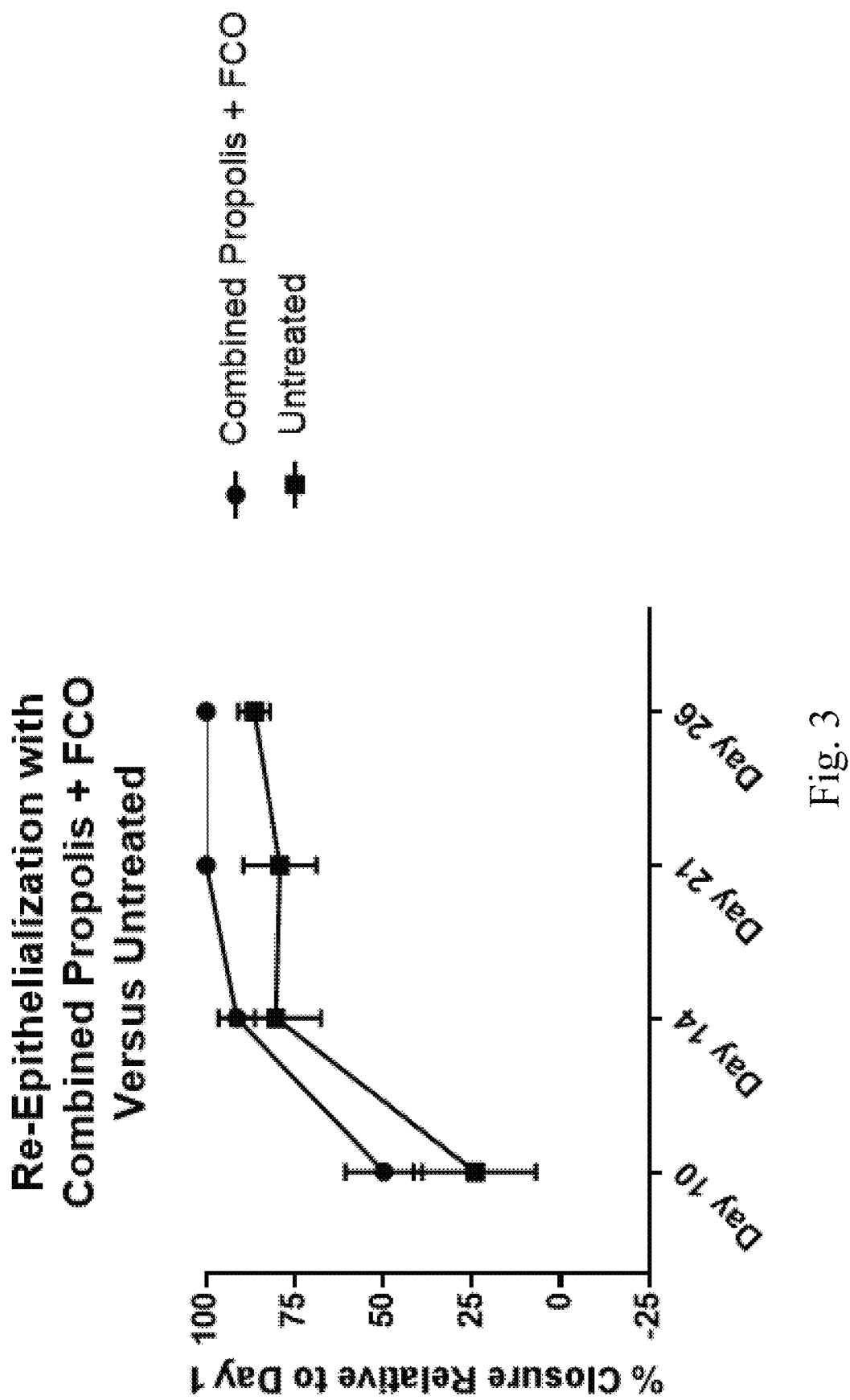
Figure 4:
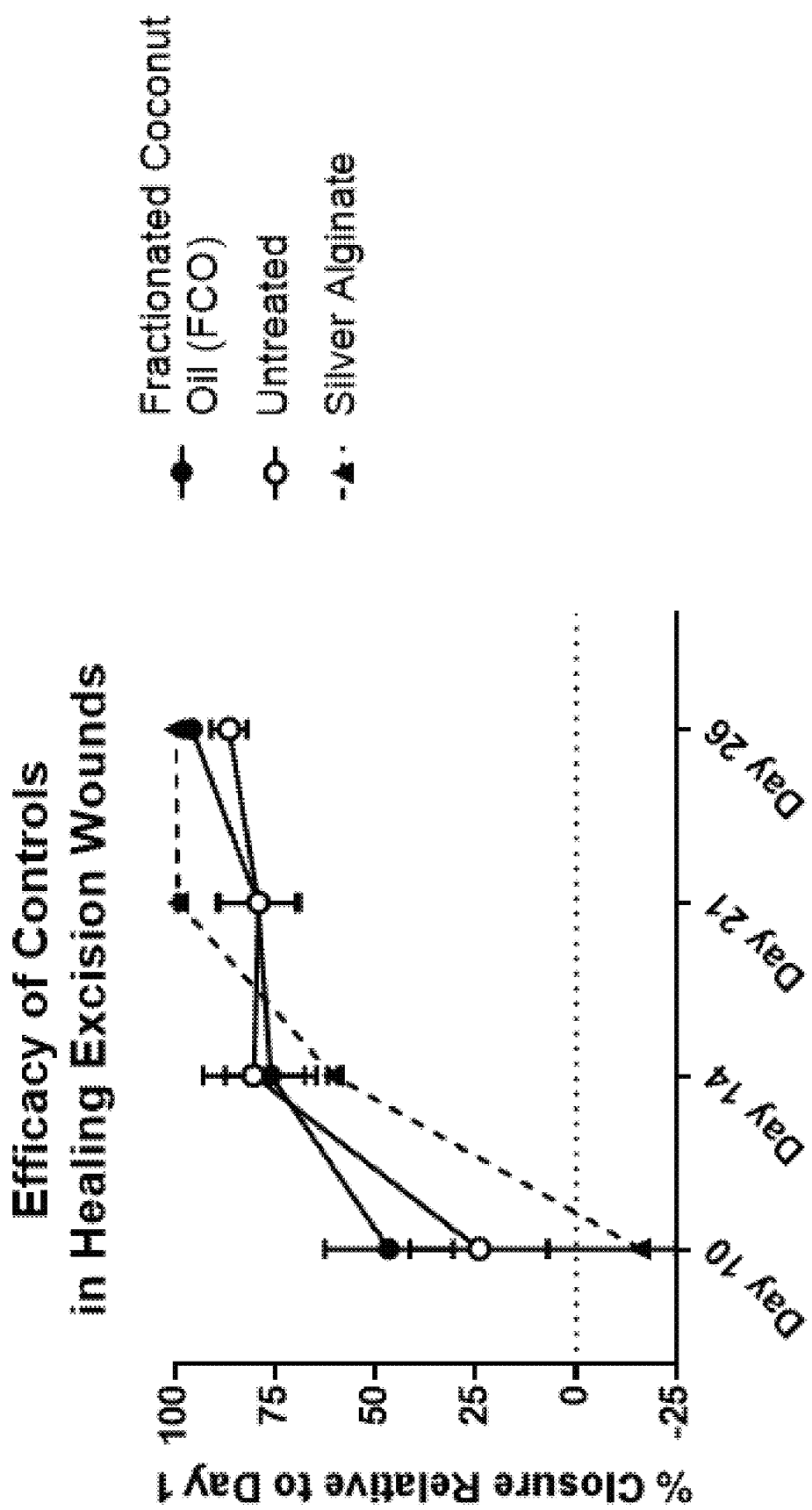
Figure 5:
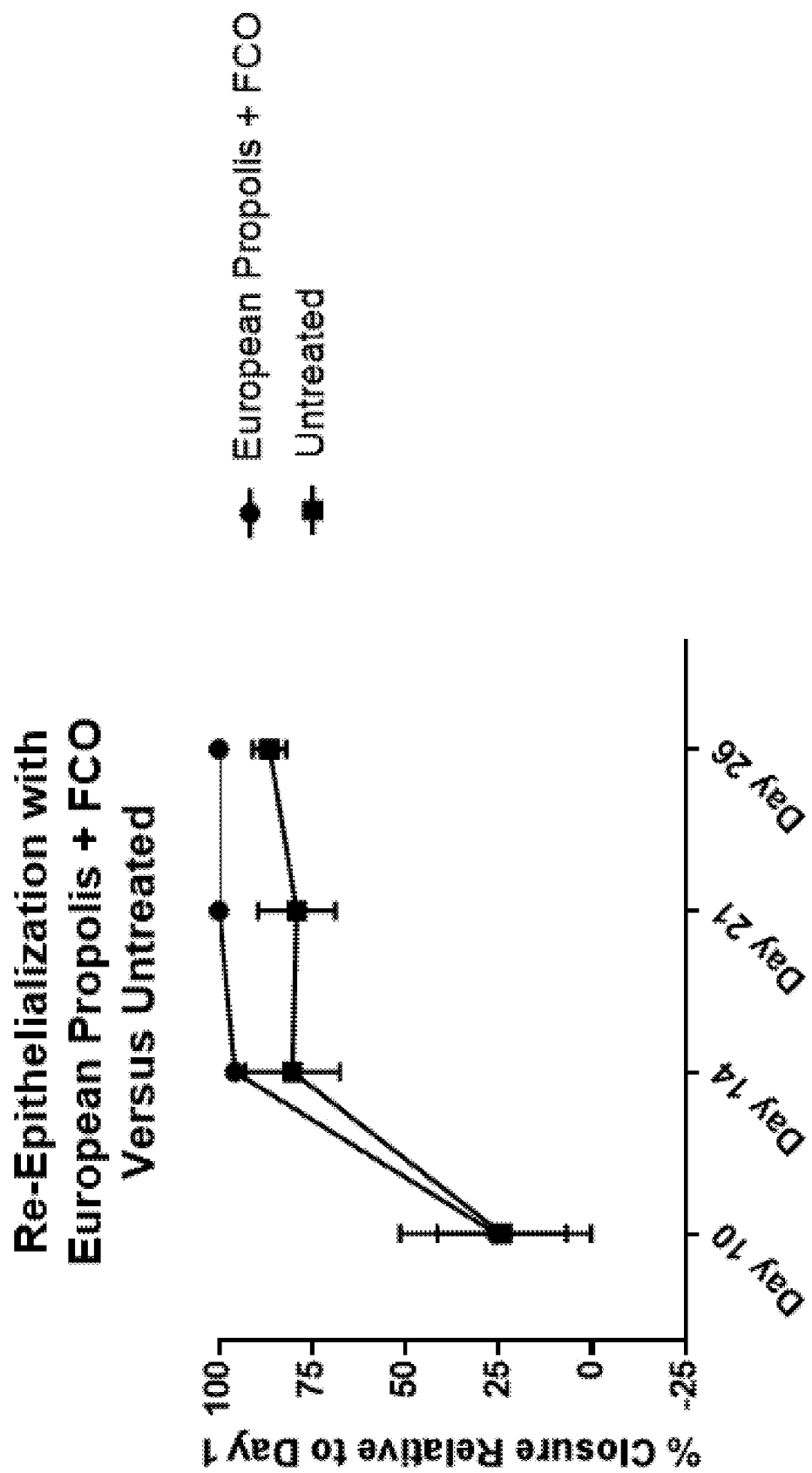
Figure 6:
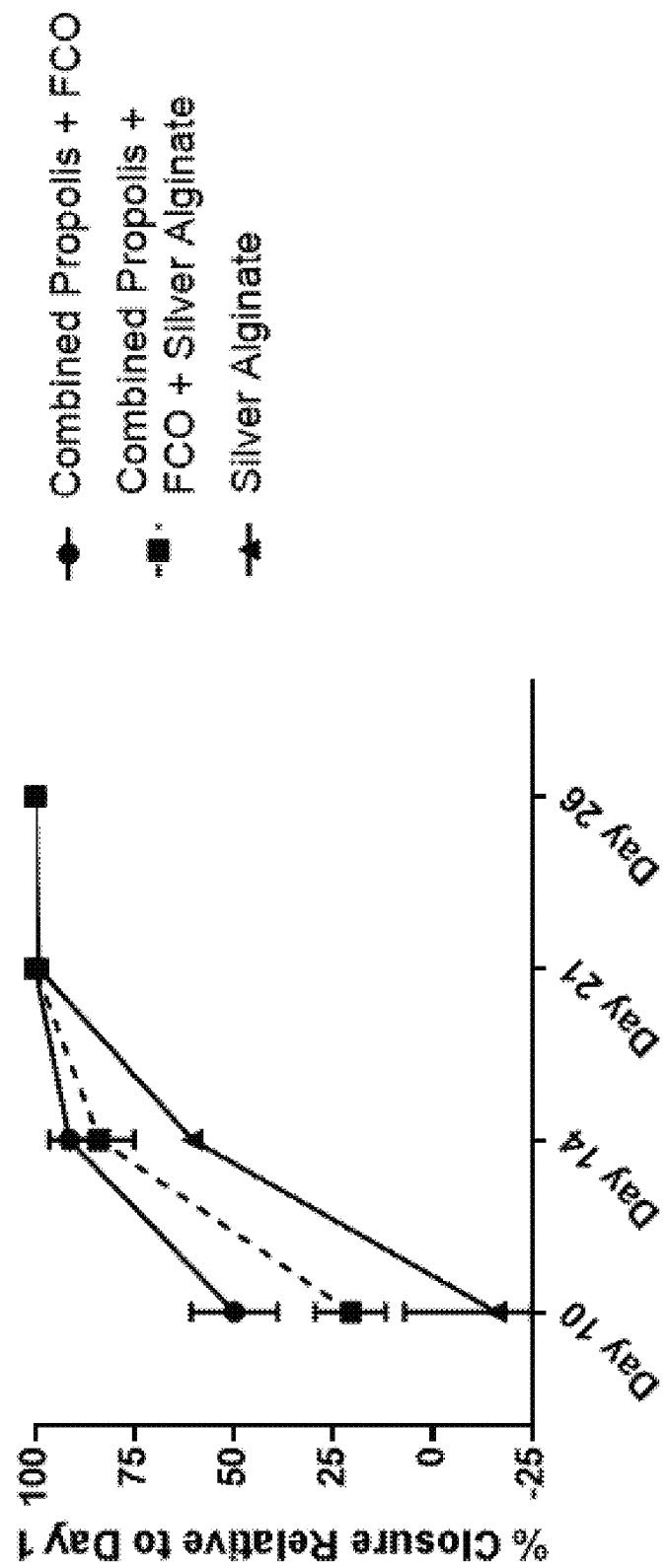

The present invention is a medicated propolis and analgesic oil that can treat a variety of wounds and can be delivered in a variety of ways. The present invention is directed primarily at treating pilonidal disease/cysts, but could be used for any wound or surgical incision, particularly those that require significant time to heal while remaining open, or those that cannot/should not be sutured closed, including, but not limited to, diabetes mellitus (DM) ulcers, decubitus pressure ulcers, open wounds with resistant bacterial infections (such as MRSA), and psoriasis.

The medicated ointment of the present invention comprises propolis, a carrier, an analgesic, a surfactant, a diluent, and can be optionally used in conjunction with a dressing and/or silver alginate. Propolis is a naturally viscous substance that results from the combination of plant exudates and bee secretions. Propolis has several therapeutic benefits, including antibacterial, antiviral, antifungal, anti-inflammatory, and antioxidant activity, as well as dermatological and wound-healing benefits. It is believed that flavonoids are the primary bioactive compounds that contribute to these therapeutic effects, with molecules such as galangin, pinocembrin, apigenin and quercetin present within propolis. Other non-flavonoid bioactive compounds include hydroxycinnamic acids, such as caffeic acid (and its derivatives) and p-coumaric acid, which have also demonstrated therapeutic effects including anti-inflammation.

The carrier can be any oil, natural or synthetic, with coconut oil preferred. The use of fatty acids, such as those present in fractionated coconut oil, as a carrier for topical wound treatments is beneficial for multiple reasons. Regarding practicality, oils add to the viscosity of a solution and are therefore more likely to remain in the wound for longer periods of time, keeping the wound moist. Furthermore, because tissue is hydrophilic, the use of oils within medicated solutions allows for a more prolonged release of active compounds into the surface area of the wound. Fractionated coconut oil is preferred in wound healing over virgin coconut oil, as this further ensures a consistent yield of predefined fatty acid chain lengths. It is important to note that the present invention uses a dry extract that is standardized to key ingredients of propolis, such as galangin, which is dissolved in solution, which means the wound tissue to be treated comes into maximum contact with solubilized, healing-enhancing compounds.

Two coconut oil fatty acids of particular interest are caprylic acid (C8) and capric (C10) acid. When attempting to treat surgical sites, cysts, or ulcers in hypoxic areas, such as the lower back or rectum, bacterial biofilms can be problematic and inhibit the healing process. Caprylic acid has shown antimicrobial activity against MRSA, MRSE, and *Pseudomonas aeruginosa*, all of which are highly drug-resistant.

Analgesic can be topical lidocaine or other commonly used topical analgesic compounds including capsaicin, amitriptyline, glyceryl trinitrate. As used herein, "analgesic" includes anesthetics and other pain killers/pain relievers. Lidocaine is a well-studied and effective method of decreasing pain experienced due to open wounds and removes the need for unnecessary discomfort due to local anesthetic injections. Furthermore, lidocaine can be paired with other active ingredients, such as epinephrine, to further increase pain relief. Aerosolized lidocaine can be used as well for treatment of surgical wounds since it is safe and effective, resulting in significantly lower pain scores and increased wound anesthesia (measured by palpation of the wound) for 24 hours after a single administration without toxic plasma lidocaine concentrations.

The surfactant can be lauryl glucoside, decyl glucoside, polysorbate 20, or polysorbate 80 or other commonly used surfactants for oil-water mixtures. Lauryl glucoside, decyl glucoside, and polysorbates 20 and 80 are non-ionic surfactants that are readily used in pharmaceutical and cosmetic products. Lauryl glucoside and decyl glucoside are made by reacting alcohols, lauryl alcohol and decyl alcohol, with glucose or glucose polymers. The resulting products work well as surfactants and emulsifiers as they consist of a hydrophobic alkyl chain attached to a hydrophilic glucose ring, both components of which are biocompatible. Polysorbate 20 (PS-20) and polysorbate 80 (PS-80) are well documented surfactants used in many parenteral drug formulations due to their biocompatibility.

The diluent can be any isotonic solution of physiological pH, with phosphate buffered saline (PBS) having a pH of about 7.4 preferred. PBS is a known diluent and is commonly used for washing/irrigating wounds due to its compatibility with tissue pH and the appropriate osmotic gradient to prevent cellular damage. PBS is also commonly used as the carrier for hydrophilic pharmaceutical compounds.

Any surgical dressing can be used, with silver alginate preferred. Silver alginate dressings are absorbent wound care products that contain sodium and calcium fibers derived from seaweed. They are typically flat dressings that are placed over open wounds, which absorb excess fluids and prevent infections. An individual dressing is typically able to absorb up to about 20 times its own weight. Alginate dressings are easy to use and can be molded to the shape of the wound, which helps ensure that they absorb wound drainage properly.

Example

A study was conducted to evaluate the healing process of full-thickness wounds treated with propolis extract in combination with fractionated coconut oil and silver alginate pads in Yucatan miniature swine. Comparisons were done between Brazilian-sourced propolis (33% w/w dry propolis extract (DPE)) in 67% w/w fractionated coconut oil (FCO), European-sourced propolis (33% DPE) in 67% FCO, a combination of Brazilian and European-sourced propolis (33% DPE) in 67% FCO, FCO alone, silver alginate (alone and with the combined propolis sample above), and untreated. The results are set forth in FIGS. 1-6.

At termination, all full-thickness wounds treated with the different propolis extract formulations, with or without silver alginate pads, were completely re-epithelialized and their wound beds completely filled with granulation tissue with accompanying notable collagen deposition of considerable maturation (whereas one untreated wound was not). Of note, there was an increase in the intensity of inflammation and/or dermatitis for the propolis-only extract-treated wounds, with or without silver alginate pads, as compared to the untreated and FCO-treated wounds (although this is likely due to the high concentration of DPE, which was chosen to identify saturating effects and possible adverse events). Propolis extract-associated inflammatory cell infiltrates were characterized by the presence of increased numbers of macrophages, lymphocytes, and multinucleated giant cells sometimes in association with remnants of putative test material. Additionally, wounds treated with silver alginate pads only were also completely filled with granulation tissue and completely re-epithelialized.

The combined propolis with fractionated coconut oil gave the best results. Including a silver alginate pad showed desirable closure rates as well. There are many varieties of propolis depending on the vegetation in the geographical area. Some studies suggest that for the most part the efficacy of healing does not vary significantly between different propolis sources. Of the samples comprising of individual DPE and FCO, European propolis performed the best, with 95% wound closure by day 14, far outperforming controls. Brazilian propolis was a dry extract (from Apis Flora) standardized to Artepillin C, and the European dry extract (from B Natural) was standardized to galangin. Any form or source of propolis could be used, but it is preferred to use a propolis dry extract that is standardized to active ingredients, examples of which include ESIT 12 from B Natural (Italy) and Premium Extra Green Propolis Powder ART 60 from Apis Flora (Brazil). Unexpectedly, combining European and Brazilian propolis showed earlier rates of epithelialization, which was close to 50% closure by day 10 vs. ~25-30% closure for other propolis and control groups.

Various embodiments and delivery methods for the invention are available, and include: medicated oil, medicated cream, medicated spray, medicated aerosol (propellants can include hydrofluorocarbons such as dichlorodifluoromethane that are commonly used in pharmaceutical mixtures, or hydrocarbons such as propane, butane, or isobutane that have low toxicity and are stronger propellants due to immiscibility with aqueous solutions), medicated microneedle patch, gel, lotion, cream, or ointment. The medicated oil is described as above. The medicated spray is similar to the oil, differing only in its viscosity by varying the carrier to diluent ratio.

The medicated oil is to be stored in a bottle with a reusable dropper. Oil can be applied directly into wound. Packaging instructions will be included on dosing information (i.e. 5-6 oil drops per application). The spray and aerosol is to be sprayed directly on wound until completely coated, after which the user should remove residual oil from healthy skin surrounding wound. Medicated oil, cream, and spray should be reapplied 1-2× daily. Medicated microneedle patch should be changed 1× daily.

The compositions of several medicated compositions follow. The components need not be mixed in the exact order given below, although the order listed might yield the best mixing results (all components listed by % w/w, and can be the exact amount listed, or "about" or "around" the amounts listed, which, as used herein, means±5%):

Medicated Oil
 1. Target 30-90% Fractionated Coconut Oil, with best rest results expected at 40-60% w/w
 2. Add 0.1-10% analgesic compound, with best results expected at 0.25-2.5% w/w
 3. Add 0.25-20% surfactants, with best results expected at 0.5-5% w/w
 4. Add 1-40% propolis, with best results expected at 5-15% w/w
 5. Add 5-50% pH-adjusted PBS, with best results expected at 10-30% w/w Medicated Cream:
 1. Target 30-90% Fractionated Coconut Oil, with best rest results expected at 40-60% w/w
 2. Add 0.1-10% analgesic compound, with best results expected at 0.25-2.5% w/w
 3. Add 0.25-20% surfactants, with best results expected at 0.5-5% w/w
 4. Add 1-40% propolis, with best results expected at 5-15% w/w
 5. Add 5-50% pH-adjusted PBS, with best results expected at 10-30% w/w
 6. Add 0.25-20% emulsifier (e.g. glyceryl monostearate, lecithin, or propylene glycol), with best results expected at 0.5-5% w/w
 7. Add 0.5-20% thickening agent (e.g. hydroxypropyl methyl cellulose (hypermellose), hydroxymethyl cellulose, hydroxypropyl cellulose, carbomer), with best results expected at 2.5-7.5% w/w Medicated Spray/Foam: (More Dilute Mixture than Medicated Oil)
 1. Target 30-90% Fractionated Coconut Oil, with best results at 30-50% w/w (more dilute)
 2. Add 0.1-10% analgesic compound, with best results at 0.25-2.5% w/w
 3. Add 0.25-20% surfactants, with best results expected at 0.5-5% w/w
 4. Add 1-40% propolis, with best results expected at 5-15% w/w
 5. Add 15-60% pH-adjusted PBS, with best results expected at 20-40% w/w (more dilute)
 6. Use standard, sterile cap capable of either producing foam (such as that seen with certain hand soaps) or spray (such as that seen with certain sunscreen or water bottles) without the use of propellants.

Medicated Aerosol:

The propellant will evaporate upon release from aerosol canister, which means that the solution contacting the exposed tissue should be of the same ingredient concentration as the medicated spray. Therefore, 20-60% medicated oil & 40-80% propellant are used, with the best results expected at 40-50% medicated oil and 50-60% propellant.

Any embodiment(s) of the medicated oil described herein may contain viscosity reducers and preservatives to prolong shelf life. These preservatives can include, but are not limited to, butyl parahydroxybenzoate, Geoguard 221, potassium sorbate, and T-50 Vitamin E Oil.

An additional embodiment includes the use of a microneedle patch. This medicated formulation uses a further diluted version of the Medicated Oil described above. The microneedle patch utilizes a drug reservoir and hollow needles, although a dissolving polymer needle system may be used. The needles pierce through the epidermis and, depending on their length, release drug into the dermis or hypodermis layers of skin. The microneedle patch system is used to treat internal wound indications (ulcers). The medicated oil, spray/foam, aerosol is used for open wounds. The microneedle composition is the same as the medicated spray with a lower viscosity to ensure passage of the oil through the hollow needles.

Another embodiment of the present invention allows for wound oxygenation by using a mesh bandage design, that serves as a strong scaffold for medicated propolis oil, and wicks away wound drainage into a cotton reservoir (in order to further reduce chances of infection). This reduces the need for heavy gauze packing in the wound. This mesh is designed to be molded/shaped into the contours of wound and stay in the wound through silver-alginate-to-wound fluid adhesion since alginate fibers are hydrophilic. Furthermore, absorption of the medicated oil in to the alginate bandage is minimal due to the low compatibility between hydrophobic and hydrophilic materials, allowing for more active ingredient availability to exposed tissues.

Figure 7:
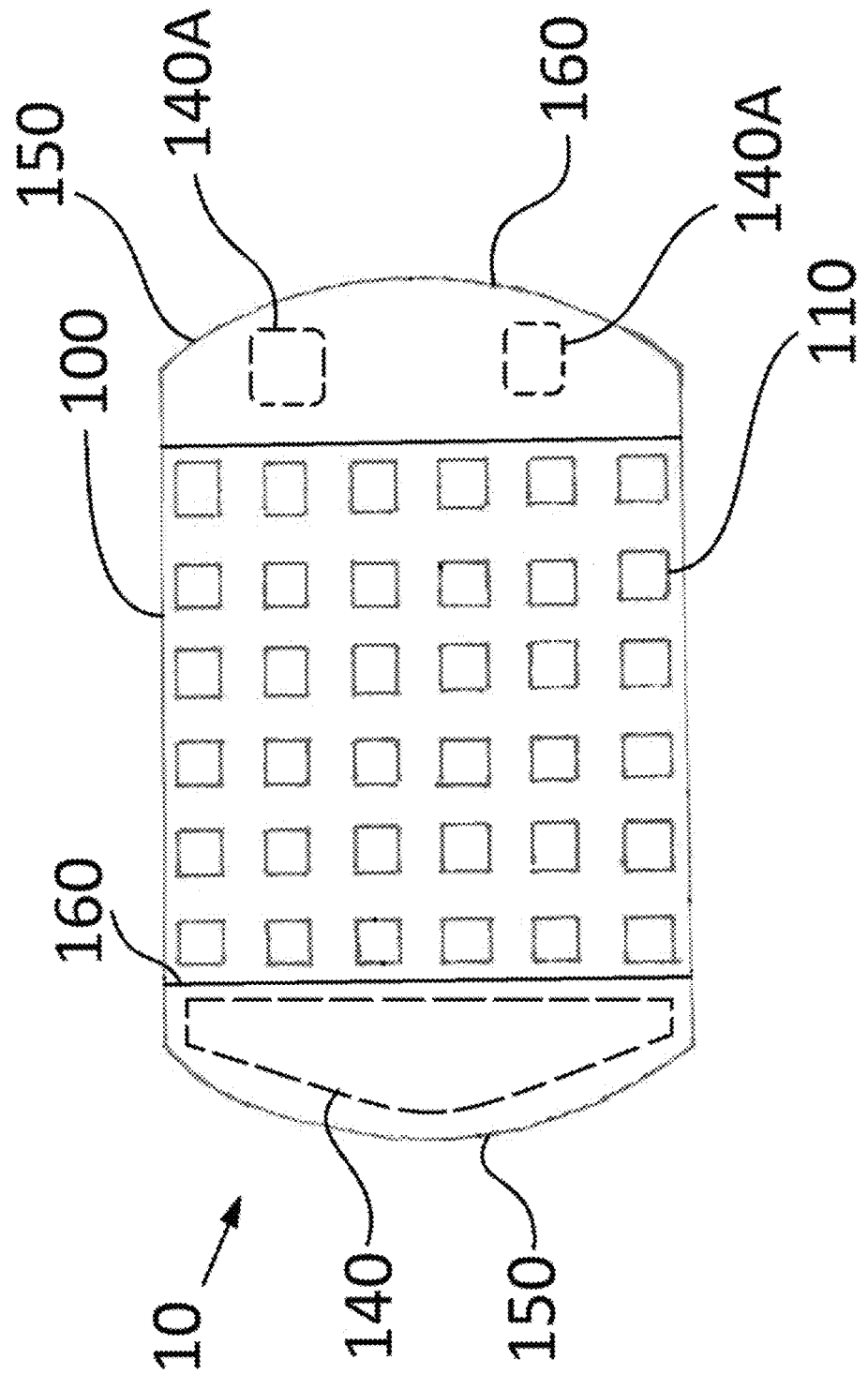
FIG. 7 is a top view of a bandage embodiment of the present invention.
Figure 8:
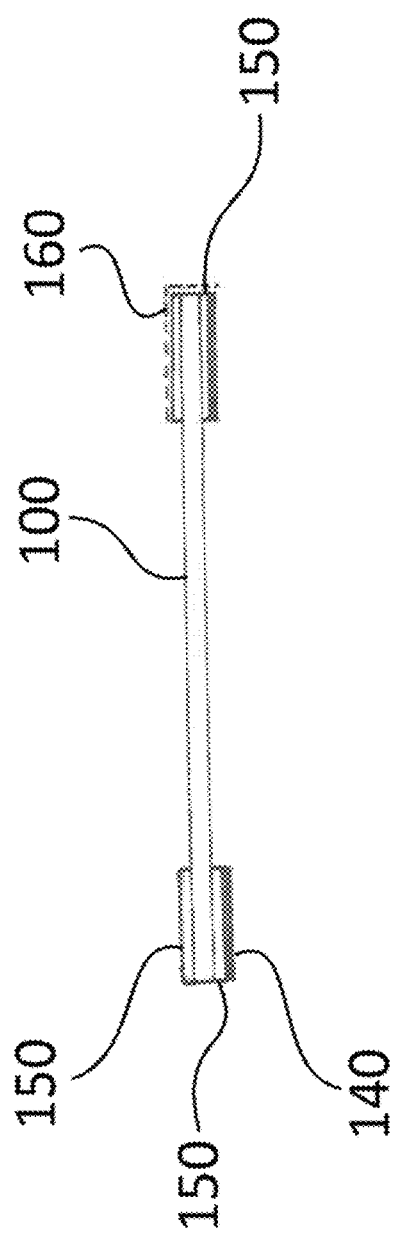
FIG. 8 is a side view of the embodiment in FIG. 7.
Figure 9:
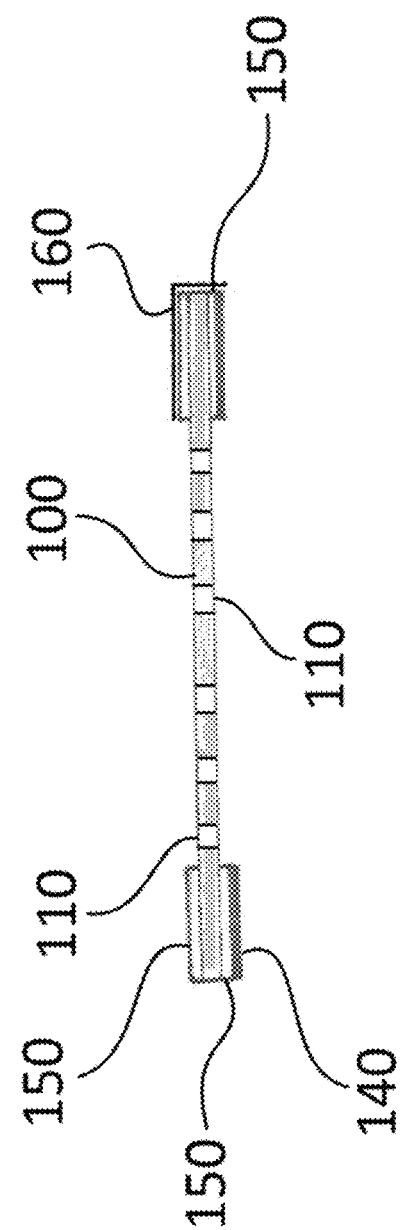
FIG. 9 is a cross-sectional view of the embodiment in FIG. 7.

The present invention includes a bandage composed of several layers as shown in FIG. 7. It comprises a mesh base 100; skin-adhesive pads 140; fluid-collection reservoirs 150; and a protective coating 160. The various components are discussed in more detail below.

The mesh base 100 is composed of silver-infused alginate mesh dressing. In order to keep the environment moist enough for tissue healing to commence, the structure must be able to swell and retain moisture, while wicking away excess moisture. A silver alginate base is used because such a composition is able to swell and retain moisture well in saline solutions, which are comparable to the ionic makeup of bodily fluids. Essentially, the goals are to remove wound drainage efficiently (via capillary action) while keeping the wound area moist to allow for healing, with the latter being the more important, as it directly correlates to healing. The mesh base 100 is a large fiber matrix rather than wick-like windings. Wick-like wound strands are disfavored since such an arrangement would reduce the matrix properties of the pad and would sacrifice the swelling capacity. Wick-like structures would reach a saturation point for capillary action more quickly and thus fail at removing fluids from the wound, which would increase chances of infection. A matrix arrangement will wick away liquids in a more controlled manner for a longer period of time, keeping the wound moist but still removing most of the fluids. Furthermore, fiber/wick design swelling can severely disrupt capillary action capacity, defeating one of the main purposes of this design. The mesh base 100 connects to, and feeds into (i.e. is in fluid communication with), another pad 150 that serves as a reservoir and allows capillary action to continue through sustained fluid movement.

In production, one embodiment uses a die to stamp full silver-infused alginate pads into a mesh design that can conform into a large incision and allows for the necessary swelling and wicking properties. Silver alginate is not naturally very flexible, but stamping a pad into a mesh allows the pad to contour to the wound more easily. The exact dimensions of the mesh 100 are not fixed. One embodiment uses a width of each alginate segment in the mesh of about 0.25-0.50 cm, with the cut-out square holes 110 in the mesh 100 being about 1 cm×1 cm.

Adhesive pads 140 keep the mesh 100 in place by adhering to the skin surrounding the incision. The adhesive can be a woven fabric, plastic (PVC, polyethylene or polyurethane), or latex strip. It may or may not be waterproof. The adhesive can be an acrylate, including methacrylates and epoxy diacrylates (which are also known as vinyl resins). The preferred embodiment of the adhesive pad 140 is a two-sided adhesive surgical tape, which will removeably adhere to the skin; that is, it will stick to the skin but is not overly difficult to remove, which allows for replacing bandages as needed, while reducing irritation commonly associated with repeated adhesion and removal of tape. When the bandage 10 is in use, it is draped over and into the wound. The adhesive pads 140 are affixed to the patient's skin on either side of the incision/wound. The adhesive pads can be one or more individual adhesive surfaces 140A, or, preferably, a single large surface 140 that has contours the same or similar to the perimeter of the bandage 10 itself.

The fluid collection reservoirs 150 are one or more absorbent cotton mesh pads that are positioned laterally on the peripheral boundary, or on each side of, and in the same plane as, the mesh base 100. The preferred embodiment has two reservoirs 150 on opposite sides of the mesh base 100, as shown in FIG. 7; but other variations are feasible, such as, for example, a large reservoir, or series of reservoirs, surrounding the perimeter or periphery of the mesh; or four tabs extending from each of the four sides of a square or rectangular mesh. These pads 150 are physically attached to (i.e. in fluid communication with) the mesh base 100 and serve as additional capillary rich material that continue the wicking of drainage for a longer period of time and serve as a reservoir for bodily fluids. The silver alginate mesh 100 and fluid collection reservoir 150 have different abilities to retain water and fluids; when the alginate mesh 100 retains more fluids than the collection reservoir 150, the fluids will move from the region of higher concentration to lower concentration (alginate to reservoir) keeping a gradient present and constant channeling into the reservoir 150 until it reaches a maximum concentration determined by its physical properties. The adhesive pads 140 are physically connected to the underside of the fluid collection reservoirs 150.

The protective coating 160 is an impenetrable layer that covers the upper side of reservoirs 150. As used herein, "impenetrable" means the bodily fluids in a wound cannot penetrate this layer. It is possible that the protective coating 160 can cover the outer layers of the bandage 10, but such a covering can limit the ability of oxygen reach the reach the wound. Therefore, it is preferred that the coating 160 covers only the reservoirs 150 to improve oxygenation of the wound. The coating 160 prevents accumulated drainage in the reservoir 150 from seeping through the bandage and soiling the patient's clothing or furniture. The coating 160 is any hydrophobic plastic layer, such as vinyl, preferably PVC.

The medicated propolis oil should be applied directly to the wound to ensure maximum coverage of tissue, followed by application of the bandage, attaching the pads to both edges of the wound on healthy skin and tucking the perforated silver alginate portion into the wound. One could apply oil/spray to the bandage before application if the patient feels they cannot adequately tell if there is full oil/spray coverage of the wound (because wounds on the back can be hard to deal with by oneself), and therefore the bandage coverage would allow for peace of mind and ensure more wound coverage.

Figure 10:
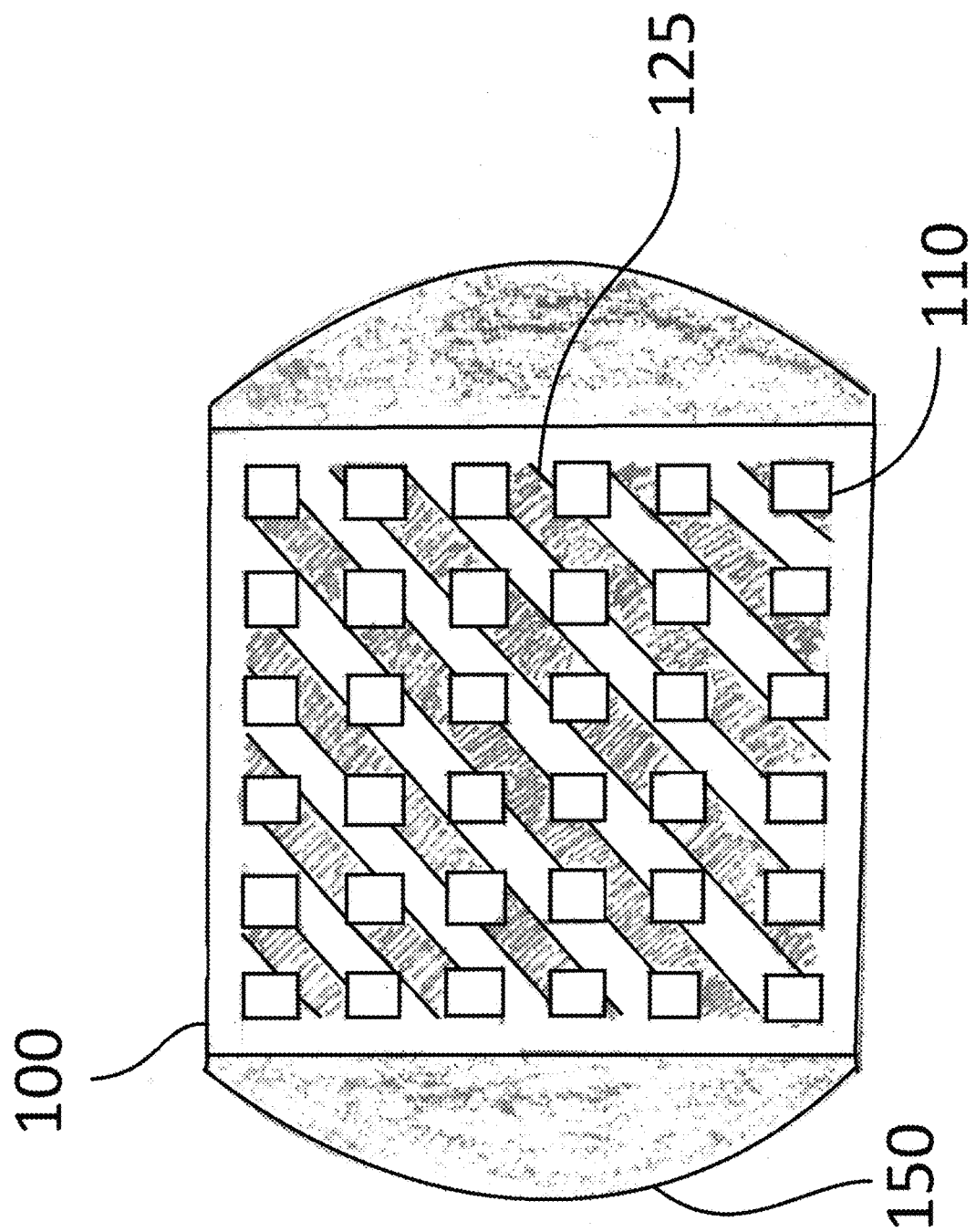
FIG. 10 is a top view of an alternate embodiment of the present invention.

An alternate embodiment comprises a variant in which the drug formulation is in the oil form described above applied directly to the bandage. The oil can be arranged in any pattern or orientation, such as completely covering the bandage, a bidirectional cross-hatch pattern, unidirectional pattern, a zig-zag/chevron pattern, etc. The preferred orientation of the oil 125 is in a unidirectional pattern, as shown in FIG. 10, which leaves space to allow for oxygenation of the wound.

In summary, the present invention can be differentiated from propolis alone by employing a carrier that provides more control for delivery, avoiding contact dermatitis by using a homogenous, controlled concentration of propolis, and finally tailoring propolis to delivery methods that take patient conditions into consideration (such as a spray for hard to reach wounds that also increases coverage of wound) and assist with pain. As noted, dissolving propolis dry extracts is difficult in solvents other than ethanol due to its high polyphenol content, and ethanol contact with exposed tissue is dangerous. Thus, what is disclosed herein is a solution that is safer than raw propolis, propolis dry extract alone, and ethanol mixtures. While some propolis extracts are water soluble, having a purely aqueous solution can pose issues due to the rapidity of uptake by exposed tissue (thereby preventing a prolonged administration of active ingredients) and/or the interruption of the integrity of hydrophilic dressings, such as those made with an alginate base.

It will be apparent to those skilled in the art that the above methods and apparatuses may be changed or modified without departing from the general scope of the invention. The invention is intended to include all such modifications and alterations insofar as they come within the scope of the appended claims or the equivalents thereof.

What is claimed is:

1. A medicated oil composition comprising
   propolis, about 1-40% by weight,
   a lipophobic carrier, wherein said carrier includes but is not limited to a fatty acid coconut oil, about 30-90% by weight,
   an analgesic, about 0.1-10% by weight,
   a surfactant, about 0.25-20% by weight, and
   a lipophilic diluent, about 5-50% by weight.

2. A medicated oil composition comprising
   propolis, about 1-40% by weight,
   a lipophobic carrier, wherein said carrier includes but is not limited to fractionated coconut oil, about 30-90% by weight,
   an analgesic, about 0.1-10% by weight,
   a surfactant, about 0.25-20% by weight, and
   a lipophilic diluent, about 5-50% by weight.

3. A medicated composition for the treatment of wounds and wound-inducing disease comprising:
   5-15% w/w propolis;
   40-60% w/w fractionated coconut oil;
   0.25-2.5% analgesic selected from the group consisting of lidocaine, capsaicin, amitriptyline, and glyceryl trinitrate;
   0.5-5% w/w surfactant selected from the group consisting of lauryl glucoside, decyl glucoside, polysorbate 20, and polysorbate 80; and
   10-30% pH-adjusted phosphate buffered saline.

* * * * *

UNITED STATES PATENT AND TRADEMARK OFFICE
CERTIFICATE OF CORRECTION

PATENT NO. : 10,888,590 B2
APPLICATION NO. : 16/042171
DATED : January 12, 2021
INVENTOR(S) : Randal Alexander Serafini, Shiv Krishnan and Jonathan Patrick Masterson, IV It is certified that error appears in the above-identified patent and that said Letters Patent is hereby corrected as shown below:

In the Claims

Column 10, Claim 1 Should Read:
1. A medicated oil composition comprising propolis, about 1-40% by weight, a lipophilic carrier, wherein said carrier includes but is not limited to a fatty acid coconut oil, about 30-90% by weight, an analgesic, about 0.1-10% by weight, a surfactant, about 0.25-20% by weight, and a lipophobic diluent, about 5-50% by weight.

Column 10, Claim 2 Should Read:
2. A medicated oil composition comprising propolis, about 1-40% by weight, a lipophilic carrier, wherein said carrier includes but is not limited to fractionated coconut oil, about 30-90% by weight, an analgesic, about 0.1-10% by weight, a surfactant, about 0.25-20% by weight, and a lipophobic diluent, about 5-50% by weight.

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*